United States Patent [19]

Ongaro

[11] Patent Number: 5,840,248
[45] Date of Patent: Nov. 24, 1998

[54] MOIST-HEAT STERILIZATION APPARATUS AND PROCESS, IN PARTICULAR TO SET UP AUTOCLAVES FOR DENTAL SURGERY USE

[75] Inventor: Daniele Ongaro, Milan, Italy

[73] Assignee: M.O.COM. S.r.L., Buccinasco, Italy

[21] Appl. No.: 634,882

[22] Filed: Apr. 19, 1996

[30] Foreign Application Priority Data

Apr. 28, 1995 [IT] Italy ................................. MI95A0852

[51] Int. Cl.$^6$ ............................... A61L 2/00; A61L 9/00; B60H 1/22
[52] U.S. Cl. ............................ 422/26; 422/38; 422/295; 422/299; 237/40
[58] Field of Search ............................ 422/26, 295, 38, 422/299; 237/40

[56] References Cited

U.S. PATENT DOCUMENTS 3,773,466 11/1973 Linder .......................................... 21/94
5,252,303 10/1993 Goof .......................................... 422/292
5,271,893 12/1993 Newman .......................................... 422/26

*Primary Examiner*—Jeffrey Stucker
*Assistant Examiner*—Hankyel T. Park
*Attorney, Agent, or Firm*—Browdy and Neimark

[57] ABSTRACT

A moist-heat sterilization apparatus is provided which comprises a boiler shell (3), a chamber (4) inside said boiler shell (3), a heating block (14) external to said chamber (4) and in contact with the boiler shell (3), a feeding circuit (12) to supply the heating block (14) with water, and a conveying circuit (26) extending between the heating block (14) and chamber (4), the heating block (14) comprising canalization members (31) interposed between the feeding (12) and conveying (26) circuits and heating members (30) adapted to create a first steam flow through the canalization members (31). The process consists in admitting a first steam flow into a boiler shell, collecting the condensation water of the first steam flow and heating the boiler shell in such a manner that a second steam flow is produced from the condensed water.

9 Claims, 3 Drawing Sheets

MOIST-HEAT STERILIZATION APPARATUS AND PROCESS, IN PARTICULAR TO SET UP AUTOCLAVES FOR DENTAL SURGERY USE

BACKGROUND OF THE INVENTION

The invention relates to an apparatus for moist-heat sterilization plant and process, in particular for autoclaves for dental surgery use.

It is known that steam autoclaves, also referred to as saturated-steam autoclaves, comprise a sterilization chamber for the objects to be sterilized which is substantially filled with saturated steam.

The sterilizing function is in fact performed by saturated steam carrying out a strong heat exchange with the material in the sterilization chamber.

The steam autoclaves for dental surgery use are distinguishable because they have small sizes, are provided with heating members defined by electrical resistors, and are capable of housing superposed trays inside which the instruments used by dental surgeons are held.

Of the autoclaves of the above type, those that are the most commonly used and have the simplest and less expensive structure are featured by having water converted to steam directly within the sterilization chamber into which cold water is admitted which is brought to evaporation by electrical resistors which have a power of about 1500 watts.

If, on the contrary, sterilization is carried out by steam generated externally of said chamber, by an external and self-contained steam generating unit, inconveniences of some importance occur for these small autoclaves.

A first drawback resides in that it is necessary to continuously execute evacuation of the water condensing within the chamber, to avoid formation of a colder mass at the chamber base.

A second drawback is represented by the fact that this external steam-generating unit causes an important loss of heat, along the steam conveying path as well Actually, an external steam-generating unit needs a power of about 2500 35 watts on an average.

Practically, strong water and electrical current consumptions occur and many complications are involved.

Conversion of water to steam carried out within the sterilization chamber does not suffer from the above drawbacks, but in this case a certain lapse of time is necessary for the admitted water to be converted to steam, which will involve a longer overall duration of the sterilization operations.

Just as an indication, an autoclave with an internal steam generation, of a volume of about fifteen litres, needs a starting time of about twenty minutes, before it reaches a steady condition and is therefore able to begin the sterilization step. This is a long time if compared with the duration of the sterilization step approximately lasting only four minutes when this operation is carried out with 205 kilopascals of pressure and at a temperature of about 134 degrees centigrade, as often happens.

Since the working time should be as quick as possible, for a prompt reuse of the sterilized material, it is apparent that this long starting time is greatly unwelcome.

In particular, the starting time to bring water to evaporation within the sterilization chamber is unwelcome and damaging in the autoclaves used in dentist's surgeries, since each delay reduces the amount of work that can be executed over a day, or involves the purchase of many specimens of all currently used instruments.

Notwithstanding the above, a relatively slow setting of the plant to a steady condition has always been considered as inevitable for the purpose of avoiding an excessive oversizing of the heating members, resulting in high installation and power supply costs and in true difficulties in the sterilization management, since with too powerful heating members it is difficult to exactly control the sterilization temperatures.

Oversizing of the heating members also brings about a loss of heat in the surrounding atmosphere and a reduced thermal efficiency and checking capability of the whole process. This is all the more true, given the fact that also with substantially non-oversized members it is difficult, in the case of internal steam generation, to achieve a uniform distribution of heat in the sterilization chamber: the lower part of the chamber easily has a different and higher temperature than the upper part thereof.

Above all, in the case of internal steam generation it is practically impossible to exploit heating members the usual electrical resistors in a continuous manner.

In fact these resistors are not subjected to a very high heat exchange with the closed environment of the sterilization chamber and therefore can easily get overheated to the point of being damaged in an irreparable manner. For this reason association of thermoregulation members with the resistors is known, so that, when the resistors get overheated, said members are capable of stopping the delivery of current to the resistors themselves for short periods of time, in order to enable a partial cooling of the latter.

SUMMARY OF THE INVENTION

The technical task underlying the present invention is to devise an apparatus and process which are capable of overcoming the above mentioned drawbacks and which, even in the presence of water to be heated within the sterilization chamber, enable the overall sterilization time to be reduced without oversizing the water-heating elements, and in addition allow a particularly careful thermal control of the heat distribution.

The technical task specified is substantially achieved by a moist-heat sterilization apparatus, in particular to set up autoclaves for dental surgery use comprising a boiler shell internally having a chamber adapted to hold objects to be sterilized, a heating block external to said chamber and in contact with said boiler shell in a manner adapted to enable a heat transmission by conduction from said heating block to said boiler shell, a feeding circuit adapted to supply said heating block with water, and a conveying circuit extending between said heating block and said chamber, said heating block internally having canalization members interposed between said feeding circuit and said conveying circuit, and heating members adapted to form a first steam flow through said canalization members.

The moist-heat sterilization process, in particular to set up autoclaves for dental surgery use, comprises at least one immediate-heating step applied to the objects to be sterilized and carried out by admitting water in the form of a first steam flow into said chamber, one condensation step, obtained by building up water resulting from condensation of said first steam flow in said boiler shell, and one sanitization step carried out by heating said boiler shell in a manner adapted to form a second steam flow from said condensation water, which second flow combines with said first steam flow, said sanitization step triggering a sterilization step on reaching predetermined pressure and temperature values in said chamber.

BRIEF DESCRIPTION OF THE DRAWINGS

The description of a preferred embodiment of an apparatus and a process in accordance with the invention is now taken with reference to the accompanying drawings, in which.

DETAILED DESCRIPTION OF THE INVENTION

Figure 1:
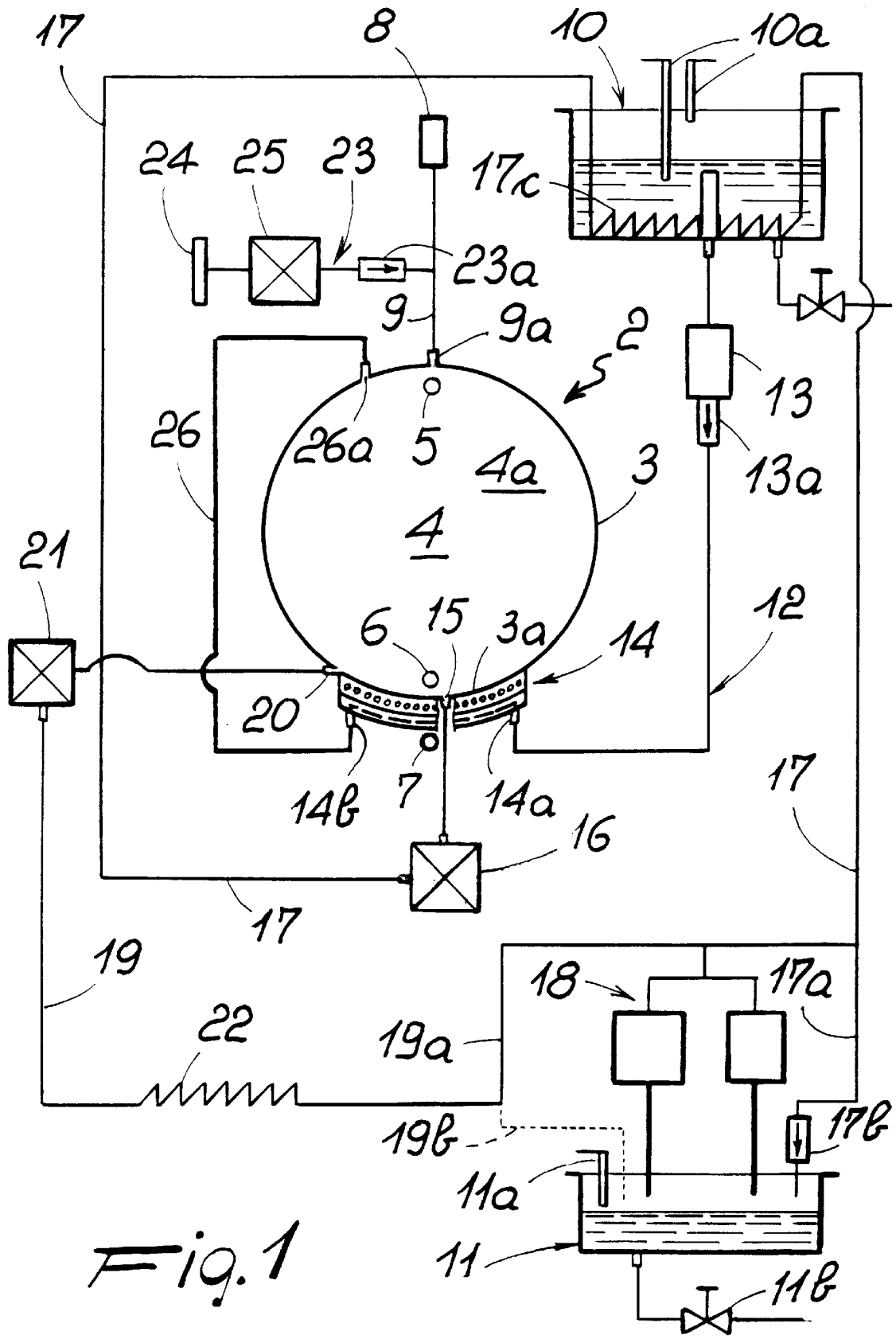
FIG. 1 shows an overall diagram of the apparatus in accordance with the invention.
Figure 2:
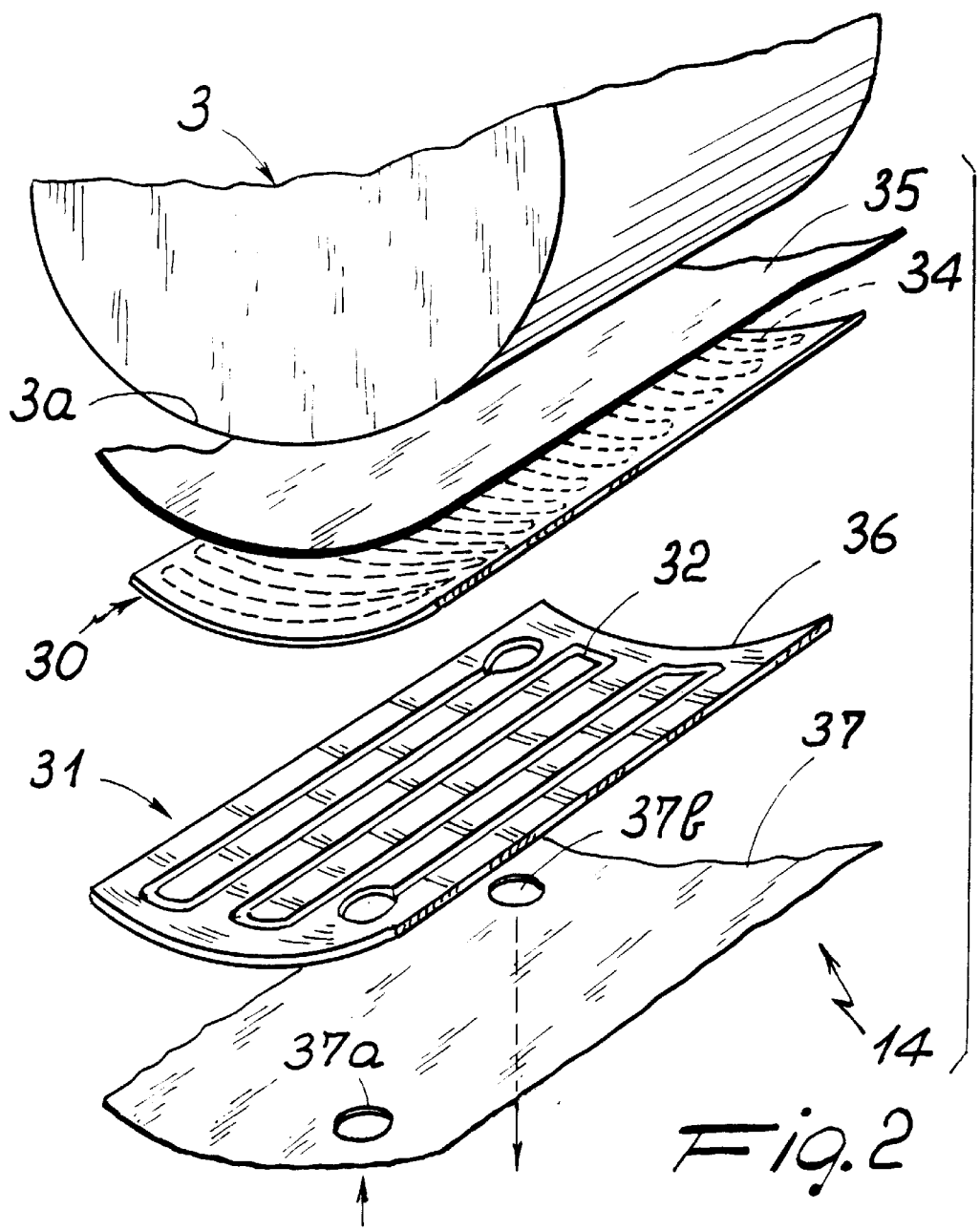
FIG. 2 is a perspective and exploded view of a steam-formation unit of the apparatus in FIG. 1.
Figure 3:
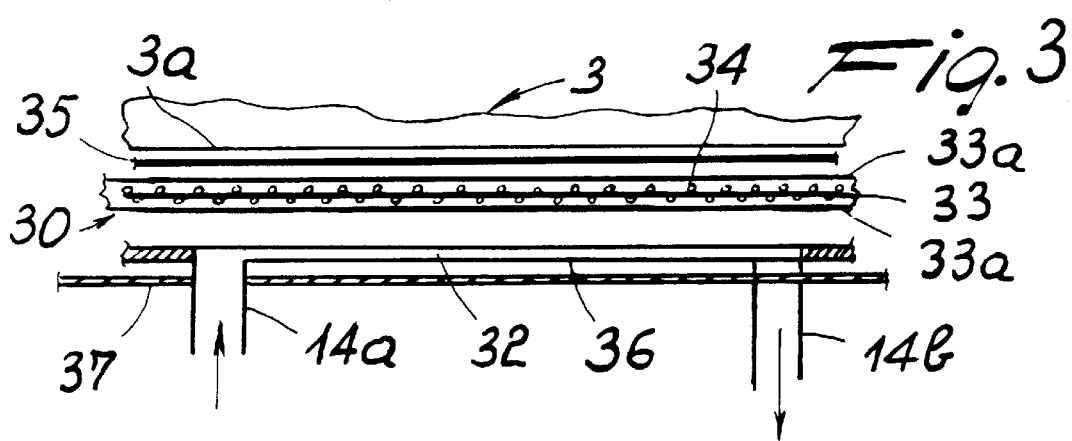
FIG. 3 is an exploded cross-sectional view of the unit shown in FIG. 2.

With reference to the drawings, the sterilization apparatus in accordance with the invention, generally embodying a saturated-steam autoclave, is identified by reference numeral 1.

It comprises a boiler 2 externally having a boiler shell 3 and internally provided with a sterilization chamber 4. A bottom area 3a is distinguisable in the boiler shell 3 and an upper area 4a is highlighted in the chamber 4.

In a manner known per se, the boiler shell 3 has at least one opening and closing door and the chamber 4 is adapted to house trays in which the objects to be sterilized are arranged.

In known manner, the boiler 2 is provided with temperature and pressure control means consisting of sensors for example, such as a first thermal probe 5 located at the upper area 4a and capable of detecting the saturated steam temperature, and a second thermal probe 6, disposed close to the bottom area 3a and capable of detecting the condensate temperature at the chamber 4 base.

Disposed externally of chamber 4, and immediately below the bottom area 3a, there is a thermal base probe 7, the function of which is to control the heating members, as better clarified in the following.

Safety devices are also provided, such as a safety valve 8 communicating via a pipeline 9 with a top hole 9a formed in the upper area of the boiler shell 3.

Several other control and safety devices known per se may be also provided, as well as members of the electronic type, known per se and not shown, for coordinating all the work steps.

The apparatus 1 comprises several members for water, steam and air circulation at the boiler 2.

Identified by 10 in FIG. 1 is a feed tank holding distilled water to be used for sterilization and by 11 a discharge tank for collection of the water used for sterilization. The distilled water in the feed tank 10 is maintained between a minimum level and a maximum level, due to the presence of two level sensors 10a, whereas a maximum-level sensor alone 11a is provided in the discharge tank 11. The tanks are equipped with drain cocks 10b and 11b at the bottom.

A feeding circuit 12 extends between the feed tank 10 and chamber 4 and it comprises members for water circulation such as a metering pump 13 capable of sending dosed amounts of water from the tank 10 to the chamber 4. Connected downstream of the metering pump 13 is a one-way valve 13a inhibiting return flows from the chamber 4 to the metering pump 13. The feeding circuit 12 opens, through an inlet 14a, into a heating block or unit 14 for heat formation, disposed in close contact with the boiler shell 3, as better clarified in the following.

A discharge circuit 17 is connected to the chamber 4 bottom at a discharge opening 15; said discharge circuit is controlled by a solenoid exhaust valve 16 and extends to the discharge tank 11, where it comprises pumping members 18 and a branch 17a provided with an exhaust valve 17b.

The discharge circuit 17 passes through the feed tank 10, upstream of the pumping members 18, where it is provided with a condenser coil 17c.

Extending from the sterilization chamber 4 are bleeding members mainly comprising a bleeding circuit 19 one end of which terminates with a bleed hole 20 and an end portion 19a of which is connected both with the pumping members 18 and the exhaust valve 17b of the discharge circuit 17.

The bleeding circuit 19 downstream of the bleed hole 20 comprises a solenoid bleed valve 21 enabling bleedings to be carried out upon command. A heat exchanger 22 is also provided downstream of the solenoid bleed valve 21, to condensate steam coming out of chamber 4.

It is also possible to make the bleeding circuit 19 directly open into the discharge tank 11, by replacing the end portion 19a with a terminal portion 19b shown in chain line in the FIG. 1.

The apparatus 1 also comprises an air-admitting circuit 23 terminating at the pipeline 9 and provided with a second one-way valve 23a.

The air-admitting circuit 23 preferably is comprised of a bacteriologic filter 24 for the external air and a compensation solenoid valve 25 controlling said air admission.

The above mentioned heating block 14 intended for steam formation is disposed at the outside of chamber 4 but in close physical contact with the bottom area 3a of the boiler shell 3, so as to enable an efficient heat conduction between the heating block 14 and the boiler area where condensate is gathered.

The heating block 14 is provided with the above mentioned inlet 14a and with an outlet 14b.

Arranged downstream of the outlet 14b is a conveying circuit 26 preferably extending in contact with the external side of the boiler shell 3 and opening into the upper area 4a of chamber 4, through a steam-admitting hole 26a.

The heating block 14 is adapted to convert to steam both the water from the circulation members 13 so as to form a first steam flow 27 conveyed into the conveying circuit 26, and the condensation water 28 gathered in the bottom area 3a of the boiler shell 3, to form a second steam flow 29.

The first steam flow 27 is substantially directed downwardly, whereas the second steam flow 29 is directed naturally upwardly.

In detail, the heating block 14 comprises substantially plate-like heating members 30, the shape of which matches that of the bottom area 3a of the boiler shell 3 at least partly, and canalization members 31.

The heating members 30 are formed of a central layer 33 on which an electrical resistor 34 of 1500 watts is wound, and two outer layers 33a of electrically insulating material, enclosing the central layer 33 and the electrical resistor 34 between them.

The canalization members 31 comprise a coil channel 32 brought into thermal conduction contact with the heating members 30.

The coil channel 32 is formed in a plate 36 in contact with the heating members 30 and is embodied by a through slot provided in the plate 36 and closed by the heating members 30 at the upper part thereof and an outer band 37 at the lower part. Practically the coil channel 32 extends through the thickness of the plate 36.

The outer band 37 has an inlet hole 37a and an outlet hole 37b for the coil channel 32 which are to be aligned with the inlet 14a and outlet 14b.

In an embodiment not shown in the figures, the coil channel 32 is defined by a plate 36 conveniently shaped and deformed so as to exhibit a coil hollow which is already closed at the lower part thereof.

If necessary, a sealing sheet made of stainless steel or another material adapted to be brought into contact with water and steam may be interposed between the heating members 30 and the coil channel 32.

At all events the heat-exchange efficiency between the heating members 30 and canalization members 31 is practically sufficiently high so as to enable the heating block 14 to be used also as a self-contained steam generator, separated from boiler 3.

In addition, preferably interposed between the heating members 30 and boiler shell 3, there is a conductive band 35 substantially extending around the whole boiler shell 3 and promoting distribution of heat from the heating members 30. This conductive band 35 is made of copper, aluminium or alloys thereof and transmits heat better than the walls of the boiler shell 3, generally made of stainless steel. Practically, the conductive band 35 Leads to a more homogeneous heating of the whole boiler shell 3. Operation of the apparatus is as follows.

After introducing the trays carrying the material to be sterilized into the chamber 4 and closing the chamber door, the pumping members 18 are turned on so that they suck the air contained in chamber 4 at least partly.

During this step the solenoid exhaust valve 16 enables suction of air through the discharge circuit 17. The solenoid bleed valve 21 is maintained open so that air can be sucked through the bleeding circuit 19 as well.

When the desired vacuum level has been reached, the solenoid exhaust valve 16 closes communication with the discharge circuit 17. The solenoid bleed valve too closes and operation of the pumping members 18 is stopped.

The metering pump 13 sends water in a dosed amount to the heating block 14, which has been previously turned on so that the heating members 30 have already reached the foreseen operative temperature when water begins passing through the coil channel 32.

Figure 4:
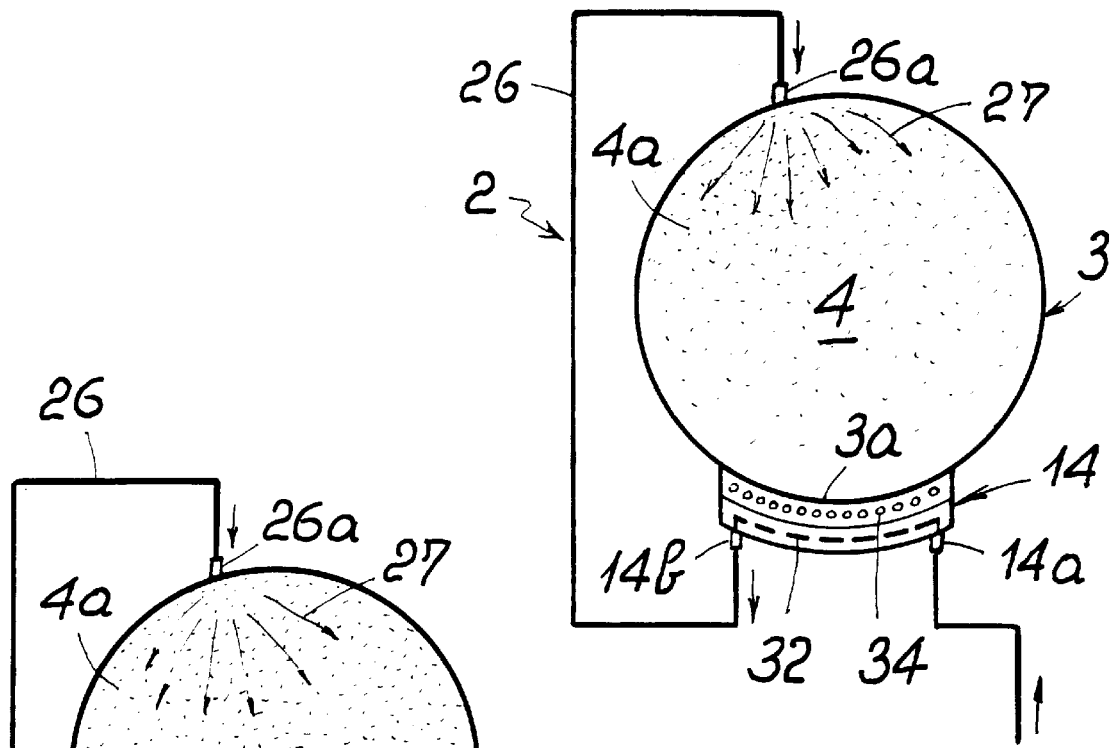

Under this situation, the water is immediately converted to a first steam flow 27 which is conveyed to the upper area 4a of chamber 4 (FIG. 4).

Figure 5:
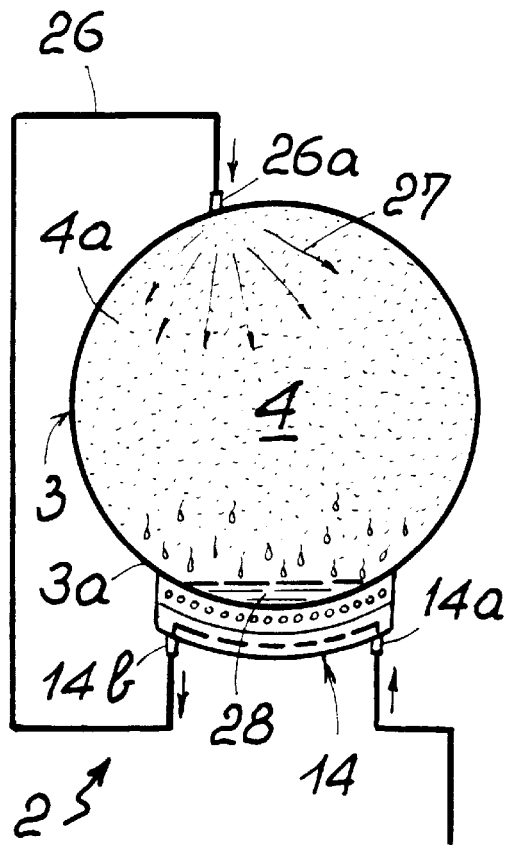
FIGS. 4, 5 and 6 show the heating step, condensation step, and sanitization and sterilization step respectively, as carried out by the apparatus of the invention.

Due to its impinging on the material to be sterilized, the first steam flow condensate at least partly and the condensation water 28 thus formed is collected in the bottom area 3a of the boiler shell 3 (FIG. 5).

Figure 6:
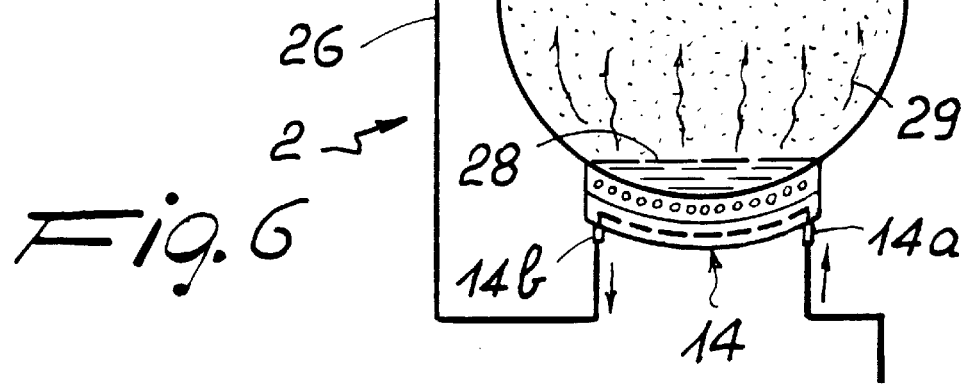

The heating block 14 however, intensely heats the boiler shell 3 as well, in that the heating members 30 are exactly in contact with the bottom area 3a of the boiler shell 3 and transfer heat thereto, so that evaporation of the condensation water 28 is caused and, as a result, a second steam flow directed upwardly is generated (FIG. 6).

There is therefore a double steam flow in two different and basically opposite directions, and this double flow enables a better sterilization of the objects arranged in chamber 4 and a more homogeneous heat distribution.

Obviously, the second steam flow 29 partially condenses too and this condensed water as well is evaporated again. Heating of the boiler shell 3 and the flow rate of the first steam flow are adjusted depending both on the temperature and pressure values to be reached in chamber 4, and the thermal conditions of the heating block 14.

As regards the temperature and pressure values to be reached in chamber 4, it is pointed out that they typically are a pressure of at least approximately 205 kilopascals and a temperature of at least 134 degrees centigrade.

As regards thermal conditions of resistor 34, it is pointed out that the thermal base probe 7 is intended for thermal control of the heating block 14 and that detections of said probe cause operation of the metering pump 13: in the presence of overheatings, the metering pump sends greater amounts of water that will give rise to an immediate cooling of the resistor 34.

Simultaneously with steam formation, several steam drainages and bleedings can be carried out through the bleeding circuit 19 and solenoid bleed valve 21, for the purpose of adjusting pressure at the inside of chamber 4 and above all discharging, together with steam, the residual air still present in chamber 4. This is in particular necessary when the temperature and pressure control devices within the chamber 4 detect temperature values noticeably different from the theoretical saturated-steam values at the same pressures. When sterilization is over, steam is discharged through the discharge circuit 17, after opening the discharge solenoid valve 16. The bleeding circuit 19 too may cooperate in discharging.

After the discharging operations, the compensation solenoid valve 25 is operated to enable admission of filtered air into the chamber 4, through the air-admitting circuit 23.

The sterilization process performed by the apparatus in accordance with the invention takes place as follows, with reference to the steps of filling the chamber 4 with steam, carried out after suction of air from the chamber itself. First of all a heating step is executed, which consists in admitting a first steam flow formed by the heating members into the chamber 4, preferably at the upper area thereof. The first steam flow preferably impinges from the top onto the objects located inside the chamber 4.

In an immediately following condensation step, said first steam flow impinging on said objects partly condenses and is collected in a bottom area of the boiler shell 3, in the form of water.

Then, a step takes place in which also the bottom area 3a of boiler 3 submitted to heating,causes evaporation of the condensation water collected therein, so as to form a second steam flow, directed upwardly.

By this second flow being produced while the first flow still lasts, a sanitization step is accomplished which is exactly characterized by the presence of two steam flows preferably moving in opposite directions and therefore capable of impinging on all the objects to be sterilized in an optimum way.

Said sanitization step initiates a true sterilization step, for example when in chamber 4 pressure and temperature values of 205 kilopascals and 134 degrees centigrade respectively are reached.

Under these conditions, the sterilization step lasts approximately four minutes.

It is provided that the same heat source acting on the bottom area of the boiler shell should also produce the first steam flow.

In addition, the first steam flow itself carries out thermoregulation of said heat source: in the presence of overheatings the first steam flow is increased so as to achieve a greater heat absorption through the same. Therefore it does not appear necessary that operation of the heating members be stopped when said members tend to become overheated.

The invention achieves important advantages.

The apparatus has a single heating block the sizes of which are selected based on the heat amount usually required for causing the water built up within the boiler shell 3 to evaporate gradually, and in addition in many respects the plant remains similar to the autoclaves forming steam inside them.

However this single heating block 14 is not only capable of heating the boiler shell 3 so as to cause evaporation of the water in chamber 4, but also of admitting this water into chamber 4 in the form of a first steam flow, which flow combines with the second flow generated by normal heating of the boiler shell 3 so as to perform a sanitizing step. In addition, the sanitizing step, on reaching appropriate pressure and temperature values, initiates a particularly efficient sterilization step, in that the presence of two steam flows of different directions leads to an improvement in sterilization and a greater homogeneity in temperatures, since the material is better impinged on by steam.

By the present invention an immediate utilization of the time during which it was previously needed to wait for the water to evaporate in chamber 4 is achieved; in addition and above all, also greatly reduced is the starting time which in the prior art was required for reaching the temperature and pressure values necessary for the sterilization step to begin.

Practical tests have shown a halving of this starting time, that therefore passes from about twenty minutes to about ten minutes. The drastic reduction of this starting time is due to the fact that the first steam flow first heats the objects and the surrounding atmosphere within chamber 4, and to the fact that the same first steam flow thermoregulates the resistor 34, by its intensity varying upon command, so that a current cut off to said resistor is always avoided even in case of overheatings.

Thermal efficiency is satisfactory too: the produced heat is almost completely absorbed, since the resistor has the boiler shell on one side and the coil channel on the other side and therefore the loss of heat in the surrounding atmosphere is minimum.

I claim:

1. A moist-heat sterilization apparatus comprising a boiler shell, a chamber defined within said boiler shell for holding object to be sterilized, a heating block located externally of said chamber and in contact with said boiler shell for transmitting heat by thermal conduction to said boiler shell, heating members in said heating block, a water feeding circuit for feeding water to said heating block, a steam conveying circuit between said heating block and said chamber for conveying steam to said chamber, said steam conveying circuit ending in said chamber at a position spaced from said heating block, and means defining a steam generating canalization within said heating block, said canalization providing communication between said water feeding circuit and said steam conveying circuit, whereby said heating means causes a first steam flow to be generated through said canalization and to be conveyed by said steam conveying circuit to said chamber and a second steam flow to be generated internally of said chamber adjacent said heating block.

2. Apparatus according to claim 1 wherein said heating members are located between said boiler shell and said canalization.

3. Apparatus according to claim 1 wherein said chamber has an upper area and said boiler shell has a bottom area, and wherein said heating block is arranged in contact with said bottom area and said steam conveying circuit opens into said chamber at said upper area.

4. Apparatus according to claim 1 further comprising a thermal base probe for temperature control in said heating block, and wherein said water feeding circuit comprises a water feed tank and a water metering pump arranged downstream of said water feed tank, said water metering pump being operationally connected with said thermal base probe for increasing the water feed to said heating block when said thermal base probe detects overheating of said heating member.

5. Apparatus according to claim 1, wherein said canalization comprises a coil-shaped channel developing within said heating block.

6. Apparatus according to claim 1 wherein said heating block comprises a first plate member and a second plate member adhering to each other, and wherein said canalization comprises a coil-shaped channel formed in said first plate member and said heating members comprise an electrical resistor carried by said second plate member.

7. Apparatus according to claim 1 further comprising a thermally conductive band inserted between said heating members and said boiler shell, said thermally conductive band enclosing said boiler shell.

8. A process for moist-heat sterilization in an apparatus having a boiler shell, a sterilization chamber within said boiler shell for holding objects to be sterilized, and heating members for generating steam for sterilizing said objects, the process comprising the steps of:

(a) generating a first steam flow outside of said chamber and admitting said first steam flow into said chamber to act on said objects wherein said first steam flow flows in a first direction;

(b) subsequently generating a second steam flow inside said chamber by causing evaporation of water resulting from condensation of said first steam flow in said chamber to form a second steam flow acting on said objects wherein said second steam flow flows in a second direction;

wherein said first direction is different from said second direction.

9. A process according to claim 8 further comprising the steps of:

(c) detecting the temperature of the heating members during generation of said first steam flow;

(d) increasing said first steam flow when said temperature detectors detect overheating of said heating members.

* * * * *